United States Patent [19]

Adjei et al.

[11] Patent Number: 5,505,194
[45] Date of Patent: Apr. 9, 1996

[54] AEROSOL INHALATION DEVICE HAVING SLIDEABLY AND ROTATABLY CONNECTED ELLIPTICAL CYLINDER PORTIONS

[75] Inventors: Akwete L. Adjei, Wadsworth, Ill.; Barbara A. Danks, Greers Ferry, Ark.; Lois R. Sherry, Lincolnshire, Ill.

[73] Assignee: Abbott Laboratories, Abbott Park, Ill.

[21] Appl. No.: 317,428

[22] Filed: Oct. 4, 1994

Related U.S. Application Data

[63] Continuation of Ser. No. 216,702, Mar. 23, 1994, abandoned.

[51] Int. Cl.$^6$ .......................... A61M 11/08; A61M 15/06
[52] U.S. Cl. .......................... 128/200.23; 128/203.23; 222/182
[58] Field of Search .......................... 128/200.23, 203.23, 128/203.18, 203.21, 203.24; 239/451; 222/398, 522, 523, 182

[56] References Cited

U.S. PATENT DOCUMENTS

| | | | |
|---|---|---|---|
| 3,151,618 | 10/1964 | Wakeman | 128/200.23 |
| 3,191,867 | 10/1964 | Helms | 239/288 |
| 3,456,645 | 7/1969 | Brock | 128/200.23 |
| 3,506,004 | 5/1970 | Mann et al. | 128/208 |
| 3,739,950 | 6/1973 | Gorman | 222/182 |
| 3,788,316 | 1/1974 | Mora | 128/200 |
| 3,918,451 | 11/1975 | Stell | 128/260 |
| 3,927,806 | 12/1975 | Meshberg | 222/402.12 |
| 3,991,761 | 11/1976 | Cocozza | 128/266 |
| 3,994,421 | 11/1976 | Hansen | 222/182 |
| 4,011,864 | 3/1977 | Guichard | 128/140 |
| 4,047,645 | 9/1977 | Caliendo | 222/398 |
| 4,069,819 | 12/1978 | Valentini et al. | 128/206 |
| 4,130,116 | 12/1978 | Cavazza | 128/203 |
| 4,227,522 | 10/1980 | Carris | 128/203 |
| 4,265,236 | 5/1981 | Pacella | 128/203.23 |
| 4,292,966 | 10/1981 | Monö et al. | 128/200.23 |
| 4,454,877 | 6/1984 | Miller et al. | 128/200.21 |
| 4,509,515 | 4/1985 | Altounyan et al. | 128/200.23 |
| 4,576,157 | 3/1986 | Raghuprasad | 128/200.23 |
| 4,637,528 | 1/1987 | Wachinski et al. | 128/200.23 |
| 4,641,644 | 2/1987 | Anderson et al. | 128/200.23 |
| 4,648,393 | 3/1987 | Landis et al. | 128/228.23 |
| 4,846,168 | 7/1989 | Abiko et al. | 128/200.23 |
| 4,860,740 | 8/1989 | Kirk et al. | 128/203.15 |
| 4,969,455 | 11/1990 | Ramella | 128/200.23 |
| 5,002,048 | 3/1991 | Makiei, Jr. | 128/200.23 |
| 5,012,804 | 5/1991 | Foley et al. | 128/200.23 |
| 5,074,294 | 12/1991 | Chiesi | 128/200.23 |
| 5,115,803 | 5/1992 | Sioutas | 128/200.23 |
| 5,134,993 | 8/1992 | van der Linden et al. | 128/200.14 |
| 5,161,524 | 11/1992 | Evans | 128/203.15 |
| 5,165,391 | 11/1992 | Chiesi et al. | 128/200.23 |
| 5,178,138 | 1/1993 | Walstrom et al. | 128/200.23 |

FOREIGN PATENT DOCUMENTS

| | | | |
|---|---|---|---|
| 1491868 | 8/1969 | Germany | 128/200.23 |
| 1128655 | 10/1968 | United Kingdom . | |
| 214246 | 1/1985 | United Kingdom . | |
| 2142246 | 1/1985 | United Kingdom | 128/203.21 |
| 2195544 | 4/1988 | United Kingdom | 128/200.23 |
| WO92/20391 | 11/1992 | WIPO . | |

Primary Examiner—Edgar S. Burr
Assistant Examiner—William J. Deane, Jr.
Attorney, Agent, or Firm—Jerry F. Janssen

[57] ABSTRACT

A collapsible, articulated actuator for the aerosol delivery of a medicament comprised comprises an elliptical expansion chamber hingedly and slideably attached to an aerosol cannister-receiving portion in a manner which permits the cannister-receiving portion to be telescoped into the expansion chamber for storage. In use, the cannister-receiving portion is pulled out of the expansion chamber and rotated until it locks into position at an angle ranging between about 102° and 110° with the expansion chamber. The angle between the two portions of the actuator, the volume of the expansion chamber, and the degree of elliptical eccentricity of the expansion chamber are optimized for maximum delivery of an aerosolized medicament to the deep lungs of a patient.

10 Claims, 4 Drawing Sheets

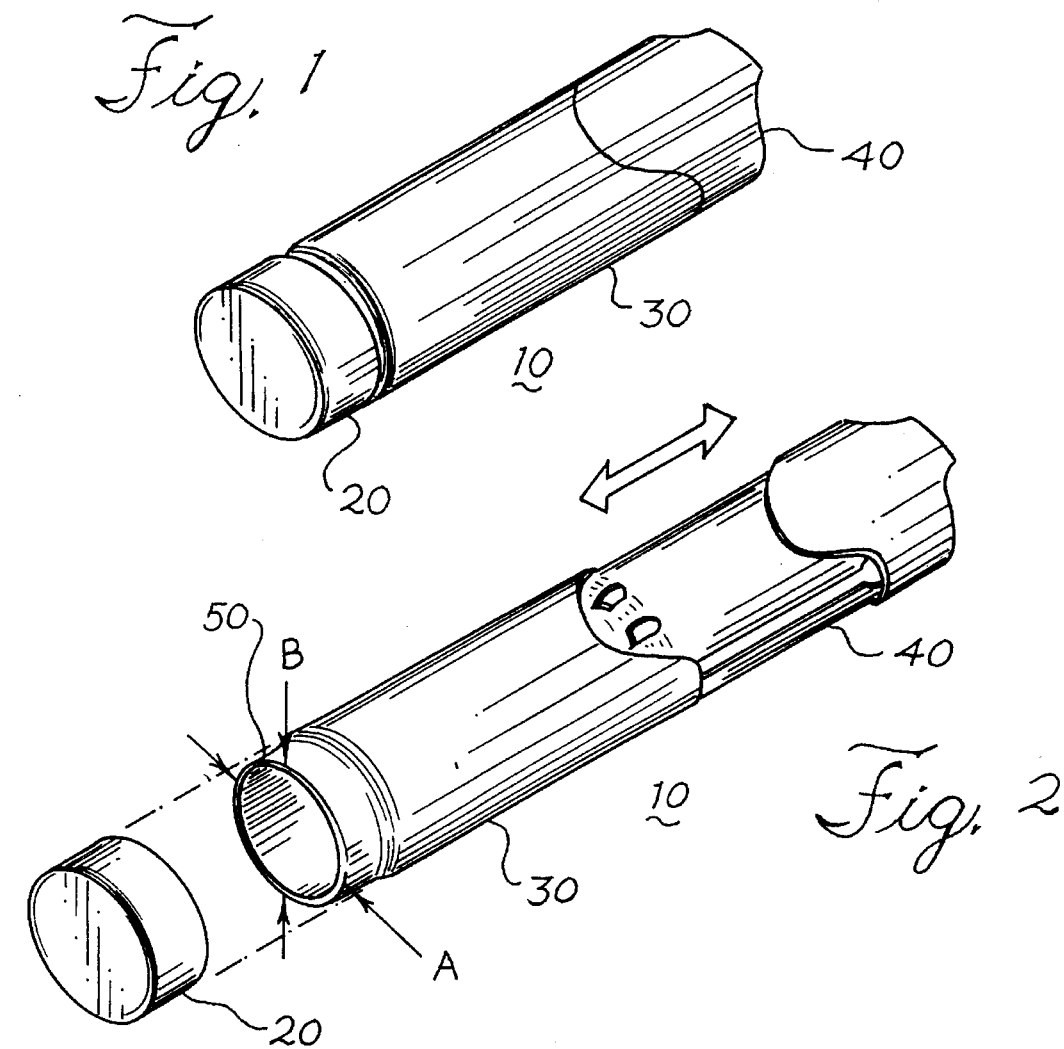
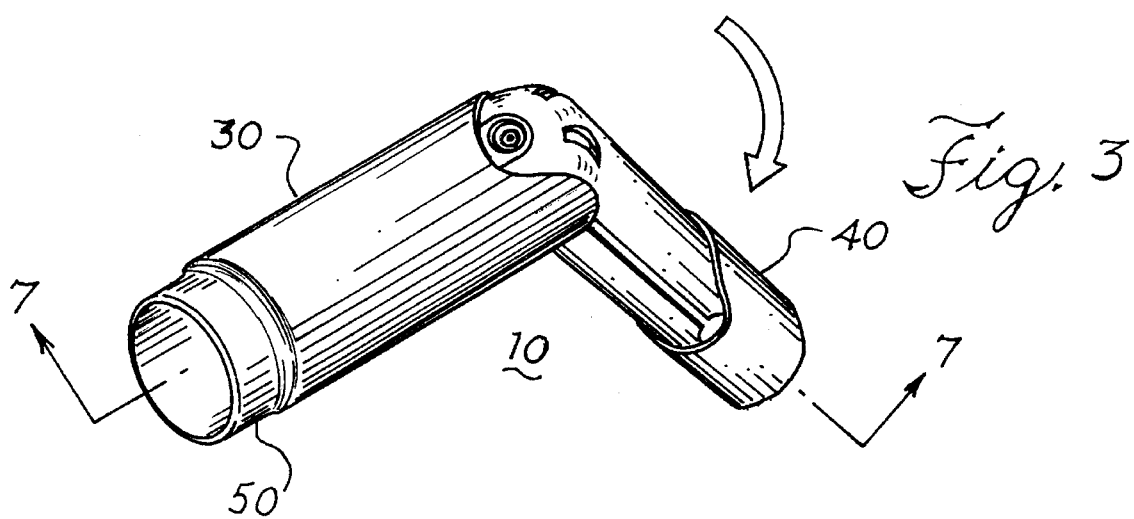

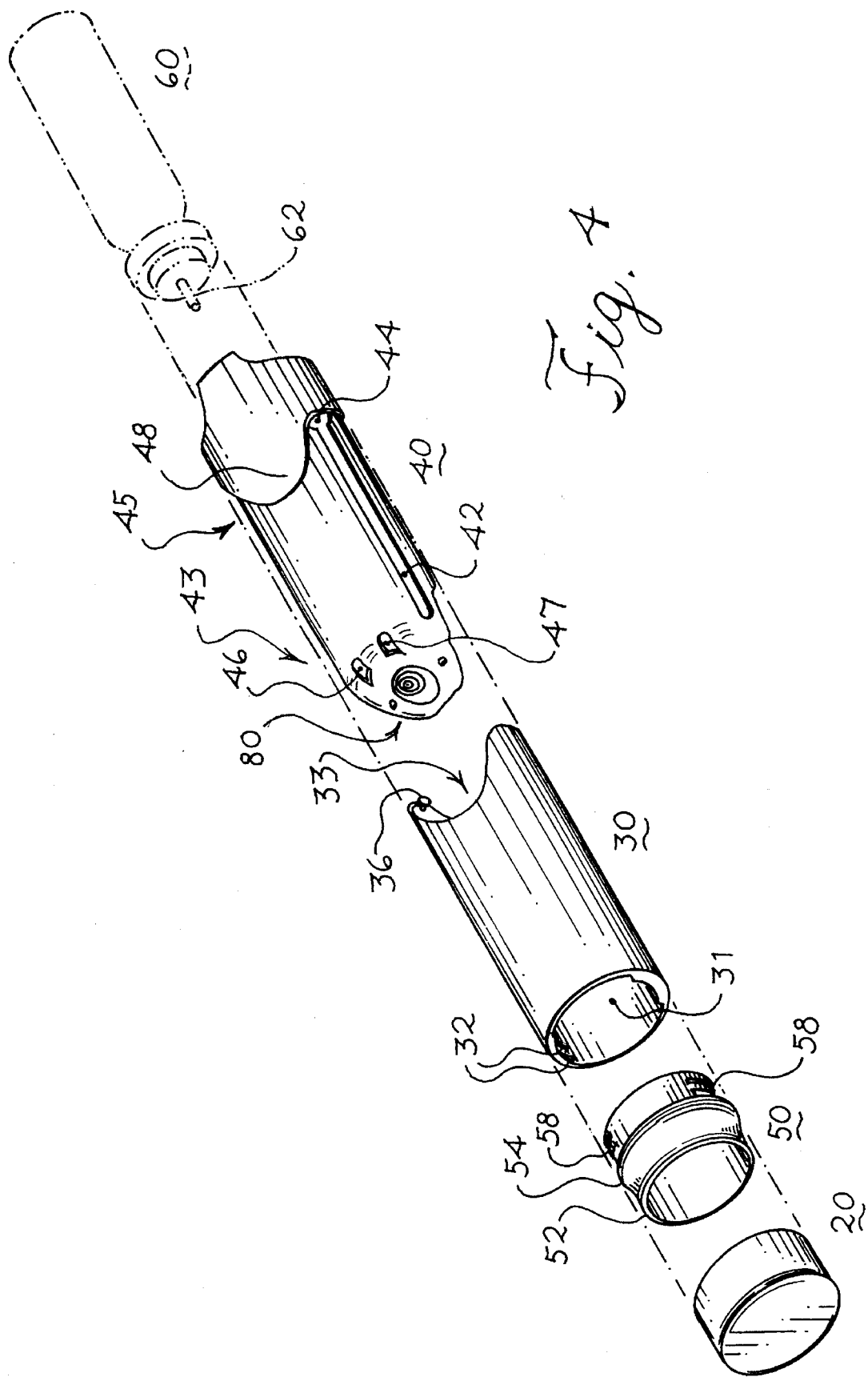

AEROSOL INHALATION DEVICE HAVING SLIDEABLY AND ROTATABLY CONNECTED ELLIPTICAL CYLINDER PORTIONS

CROSS-REFERENCE TO RELATED APPLICATIONS

This application is a continuation of application Ser. No. 08/216,702, filed Mar. 23, 1994, now abandoned.

TECHNICAL FIELD

This invention relates to medical devices. More particularly, it concerns a collapsible, articulated inhalation device for the aerosol administration of therapeutic agents.

BACKGROUND OF THE INVENTION

The administration of therapeutic agents by aerosol means is well known in the art and a number of aerosol inhalation devices are known (see, for example, Chapter 92, "Aerosols" in *Remington's Pharmaceutical Sciences* 18th Edition, pages 1694–1712, Mack Publishing Co., Easton, Pa., 1990). Fixed aerosol actuator devices of one-piece construction of the type, for example, disclosed in U.S. Pat. Nos. 3,918,451; 3,991,761; 4,011,864; 4,069,819; 4,227,522; 4,265,236; 4,454,877; 4,576,157; 4,648,393; 4,860,740; 5,002,048; 5,012,804; 5,115,803; 5,134,993; 5,134,993; 5,161,524; and 5,178,138 are well known.

Devices which are articulated and which can be folded or telescoped for convenient carrying in a pocket or purse have also been described in the prior art. Devices of this type are disclosed in U.S. Pat. Nos. 3,739,950; 3,788,316; 3,927,806; 3,994,421; 4,130,116; 4,292,966; 4,509,515; 4,637,528; and 4,641,644.

For the most part, these devices are of a design which does not address a problem with aerosol inhalation actuator devices; namely, the retention of considerable amounts of the aerosol particulates in the expansion chamber of the device or in the throat of the patient when each dose of medicament is delivered.

Sioutas (U.S. Pat. No. 5,115,803) discusses the problem, and discloses a fixed-type aerosol actuator in which the cannister-receiving portion of the device and the exit chamber are at right angles to one another, connected by a chamber having a spherical internal surface.

BRIEF DESCRIPTION OF THE DRAWING

In the drawing, which comprises a part of the description of the present invention:

FIG. 1 is a perspective view of the aerosol inhalation device of the present invention shown in its fully collapsed position.

FIG. 2 is a perspective view of the aerosol inhalation device of the present invention shown in its extended linear position with the cap shown as removed in a partially exploded view.

FIG. 3 is a perspective view of the aerosol inhalation device of the present invention shown in its fully extended and folded position for use by a patient.

FIG. 4 is an exploded view of the aerosol inhalation device of the present invention showing an aerosol medicament cannister in ghost view.

DETAILED DESCRIPTION

Figure 5:
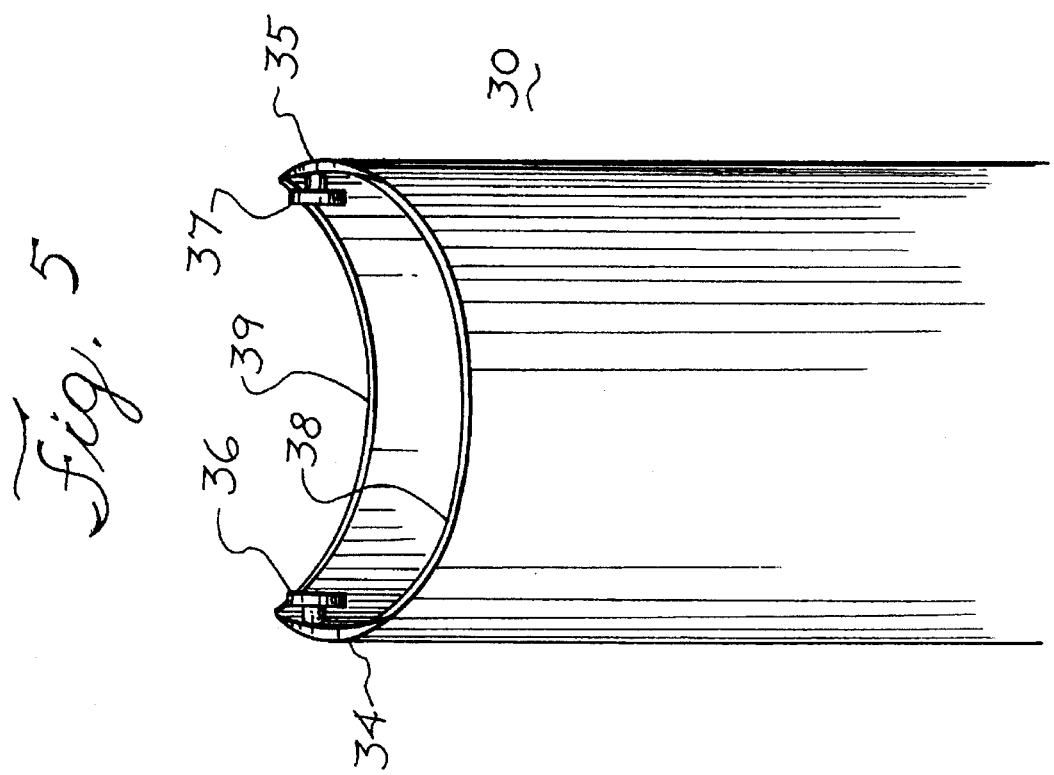
FIG. 5 is a detailed partial view of the end of the expansion chamber portion of the aerosol inhalation device of the present invention which is adapted to receive the cannister receiving portion.
Figure 6:
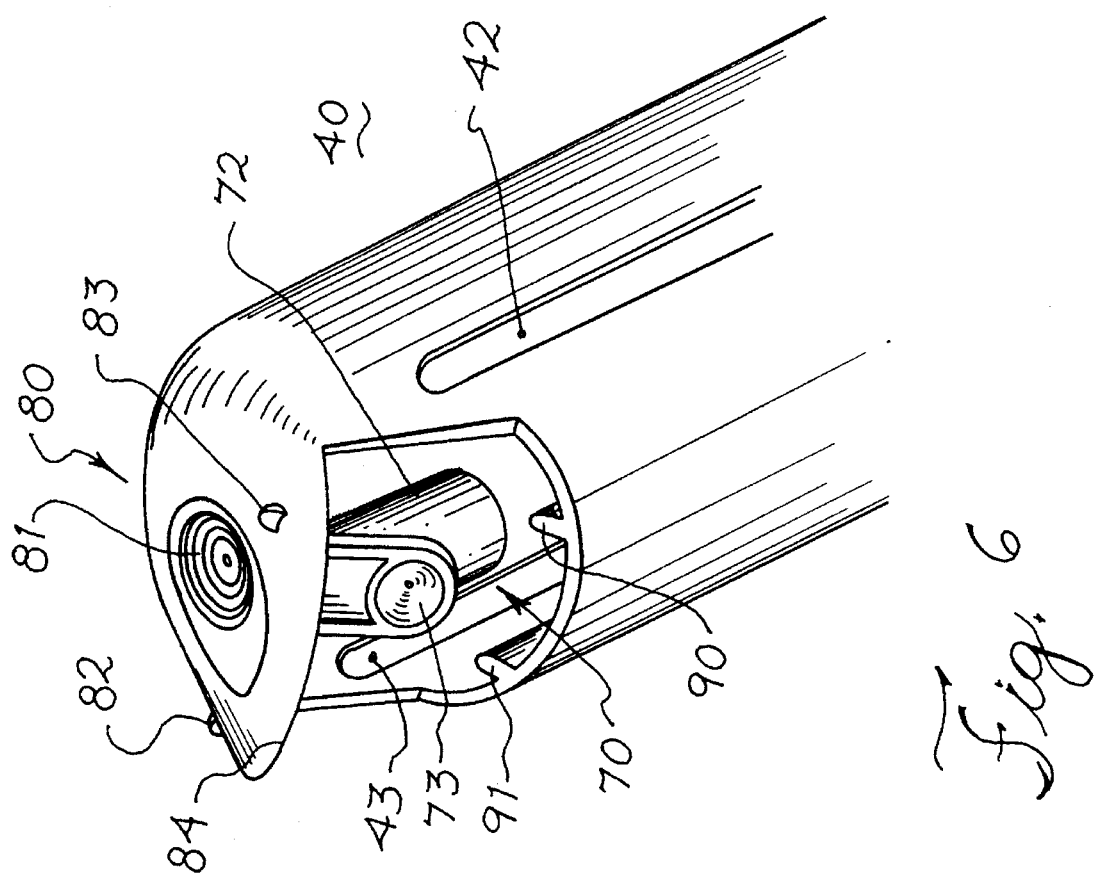
FIG. 6 is a detail partial view of the upper end of the cannister-receiving portion of the aerosol inhalation device of the present invention.
Figure 7:
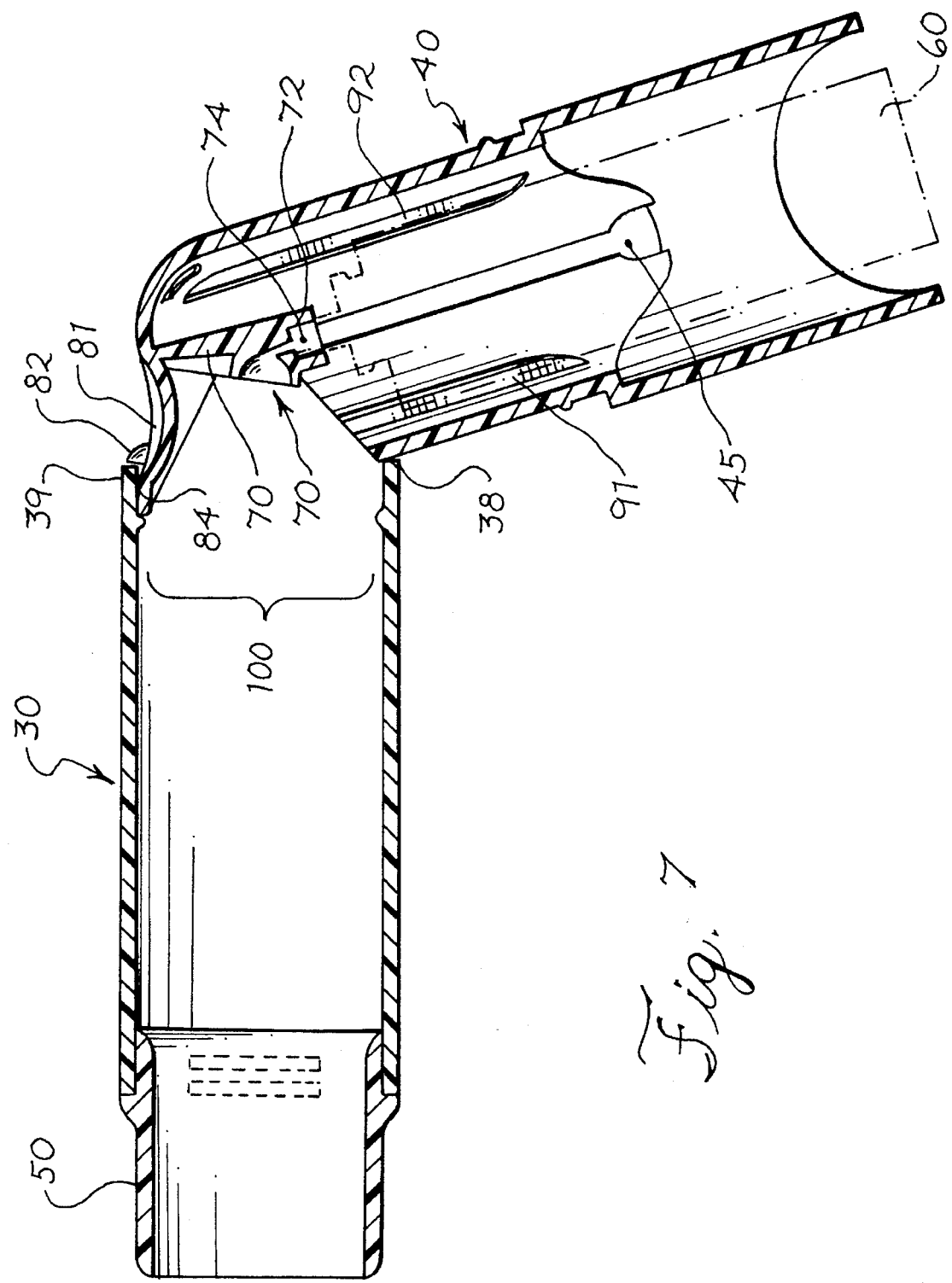
FIG. 7 is a a cut-away view, along line A—A of FIG. 3, of the aerosol inhalation device of the present invention in its folded position.

Referring to the drawings, there is shown in FIGS. 1, 2 and 3, an aerosol inhalation device in accordance with the present invention. In FIG. 1, the device 10 is shown in its fully collapsed position in which it may be conveniently carried in a purse or pocket by a patient requiting its use. The device comprises, in this view, three portions or parts: a cap 20 which fits snugly over the mouthpiece end of the expansion chamber portion or part 30, and a cannister receiving portion or part 40 shown in FIG. 1 fully retracted into the expansion chamber portion 30. The device is fabricated, most conveniently out of a plastic, such as polyethylene, polypropylene, polyvinyl chloride, or other easily molded material by conventional injection molding processes known in the art.

In FIG. 2, the aerosol inhalation device 10 is shown in its fully extended linear position in which the the cannister-receiving portion 40 has been pulled fully out of the expansion chamber portion 30. As is discussed more fully below, the canister-receiving portion 40 is slideably received in the expansion chamber portion 30, by means of slots in the cannister-receiving portion 40 which hinging means on the inner wall of the expansion chamber portion 30. The cap portion 20 is shown removed from the mouthpiece portion 50 in the end of the expansion chamber portion 30 in the partially exploded view in FIG. 2.

In FIG. 3, the aerosol inhalation device 10 of the present invention is shown, with the cap removed, in the folded position in which it is used by the patient. As is discussed more fully below, the cannister-receiving portion 40 hinges on the means disposed on the inner wall of the expansion chamber portion 30 and latches into place by stop means disposed on the upper end of the cannister-receiving portion 40.

Referring to FIG. 4, the details of construction of the the aerosol inhalation device 10 of the present invention can be more clearly seen where the device is shown in disassembled exploded view together with a medicament cannister 60 in ghost view. The device comprises four portions or parts: a cap 20, a mouthpiece portion 50, an expansion chamber portion 30, and a cannister-receiving portion 40.

The cap 20 comprises an elliptical cylinder, which is closed at one end and open at the other end and configured to be slideably received over and to form a snug friction fit with the open end 52 of the mouthpiece portion 50.

The mouthpiece portion 50 comprises an elliptical cylinder open at both ends and adapted at one end to be slideably received within the cap portion 20. The other end of the mouthpiece portion 50 is adapted to be received slideably within and to form a snap fit with the mouthpiece-receiving end of the expansion chamber portion 30. The outer walls of this end of the mouthpiece portion 50 have detents which correspond to and receive raised ridges 32 disposed on the inner wall of the expansion chamber 30 when the two portions are snap-fitted together. Engagement of the ridges 32 on the inner wall of the expansion chamber 30 and the detents 58 on the outer wall of the mouthpiece portion serve to firmly engage the mouthpiece portion 50 in the end of the expansion chamber 30 when the two portions are snapped together.

The expansion chamber 30 comprises an elliptical cylinder having an open end 31 adapted to slideably receive the mouthpiece portion 50 and to form a tight snap-fit with the mouthpiece portion 50 by means of the engagement or the ridges 32 disposed on the inner wall of the expansion chamber portion 30 and the detents 58 disposed on the outer wall of the mouthpiece portion 50 as described above. The expansion chamber portion 30 is adapted to fit over and to slideably receive the cannister-receiving portion 40 at its opposite end 33. This end of the expansion chamber 30 is shown in greater detail in the partial view in FIG. 5 where the end of the expansion chamber 30 adapted to slideably receive the cannister-receiving portion 40 is shown in a partial view. This open end of the expansion chamber portion 30 is molded in a saddle shape forming two raised hinging regions 34 and 35 in the walls of the elliptical expansion chamber 30 disposed opposite to one another along the major axis of the elliptical cross-section of the expansion chamber cylinder. Between the hinging regions 34 and 35 this end of the expansion chamber 30 is formed in curved edges 38 and 39 which, together with the hinging regions 34 and 35 form the saddle-shaped end of the expansion chamber 30 referred to above.

Hinge pins 36 and 37 are disposed on the inner wall of the expansion chamber 30 at the hinging regions 34 and 35. The hinge pins 36 and 37 comprise a short shaft and head in the manner of a common carpentry nail and are received in slots in the cannister-receiving portion 40.

Referring again to FIG. 4, the cannister-receiving portion 40 of the aerosol inhalation device of this invention, comprises an elliptical cylinder open at both ends of a size and shape to be smoothly and slideably received inside the elliptical expansion chamber 30. One end of the cannister-receiving portion 40 is adapted to receive a cannister 60 containing a pressurized aerosol medicament. The opposite end of the cannister-receiving portion 40 is open but partially, covered by a hood or knee-cap region 80. The cannister-receiving portion 40 is adapted to be slideably received within the elliptical cylinder forming the expansion chamber portion 30 and has a slot 42 disposed laterally along the side of the cannister-receiving portion 40 and a corresponding slot 43 of the same configuration lying laterally along the opposite side of the cannister-receiving portion 40 (not visible in this view). The two slots lie along the two sides of the cannister-receiving portion 40 with the central axis of each of the two sloes lying in the plane of the major axis of the elliptical cannister-receiving portion 40.

The slots 42 and 43 each have an enlarged regions 44 and 45 (not visible in this view) which receive the heads of the hinge pins 36 and 37 disposed on the inner walls of the hinging regions 34 and 35 of the expansion chamber 30 when the expansion chamber 30 and cannister-receiving portion 40 are fitted together at the time of fabrication. Openings or apertures 46 and 47 disposed in the hood or knee-cap portion 80 of the cannister-receiving portion 40, permit the flow of air into the aerosol inhalation device to dilute the stream of aerosol spray when the device is actuated.

Referring now to FIG. 6, there is shown a detailed partial view of the end of the cannister-receiving portion 40. The slots 42 and 43 which receive the hinge pins 36 and 37 disposed on the inner walls of the expansion chamber 30 can be seen in this view. A depression 81 in the outer surface of the hood or knee-cap portion 80 of the cannister-receiving portion 40 provides a finger-grip when the patient actuates the aerosol device as is discussed in further detail below. A curved lip portion 84 of the hood or knee-cap portion 80 of cannister-receiving portion 40 functions as a stop means for affixing the angle between the cannister-receiving portion 40 and the expansion chamber portion 30 when the device is in its folded position ready for use as shown in FIG. 3. Ears 82 and 83 disposed on the outer surface of the hood or knee-cap portion 80 of the cannister-receiving portion 40 function to hold the cannister-receiving portion 40 and expansion chamber portion 30 firmly in the folded position in a manner described in detail further below.

An aerosol head 70 is formed integrally with the inner wall of the hood or knee-cap portion 80 of the cannister-receiving portion 40. The aerosol head 70 comprises a cannister valve-stem receiving portion 72 and an aerosol spray orifice portion 73. As can be seen in the cut-away view in FIG. 7, a central conduit 74 for the flow of medicament passes axially through the valve-stem receiving portion 72 and the spray orifice 73 of the aerosol head 70.

Raised ridges or stand-offs 90 and 91 are disposed on the inner wall of the cannister-receiving portion 40 and function to slideably receive and firmly engage the cannister of medicament 60 within the cannister-receiving portion 40.

Referring now to FIG. 7, there is shown a cut-away view of the inhalation device of this invention in its folded position ready for use by a patient (also shown in FIG. 3). In this view the ridges or stand-offs 91 and 92 which receive and engage the cannister bottle 60 are clearly shown. Also, in this view, the means by which the cannister-receiving portion 40 and the expansion chamber portion 30 are held in firm relationship in the folded position during use are also clearly shown. When the device is used, a cannister 60 of medicament is inserted into the cannister-receiving portion 40 and the cannister-receiving portion 40 is fully retracted from the expansion chamber 30. The two portions are folded until the curved lip portion 84 of the hood or knee-cap portion 80 of the cannister-receiving portion 40 abuts the inner surface of the expansion chamber 30. At this point the opposite outer wall of the cannister-receiving portion 40 abuts the curved surface 38 of the expansion chamber 30. Further rotation of the cannister-receiving portion 40 and the expansion chamber 30 with respect to one another is thus prevented. At this point the ears 82 and 83, disposed on the outer surface of the hood or knee-cap portion 80 of the cannister-receiving portion 40 snap out and abut the curved surface 39 of the expansion chamber 30 locking the cannister-receiving portion 40 and expansion chamber protion 30 in the proper folded position with respect to one another.

In using the inhalation device of the present invention, the patient inserts the cannister of medicament 60 into the lower open end of the cannister-receiving portion 40 of the inhalation device and pushes it in until the valve-stem 62 of the cannister 60 is inserted into the valve-stem receiving portion 72 of the aerosol head 70. A tight friction fit between the valve-stem 62 of the cannister 60 and the central conduit 74 of the valve-stem receiving portion 72 of the aerosol head 70 firmly engages the cannister 60 to the inhalation device. The cannister-receiving portion 40, now containing the cannister of medicament, is pulled slideably out of the expansion chamber 40, hingedly rotated, and locked into position for use. The cap is removed and the mouthpiece portion 50 placed in th patient's mouth, holding the device in one hand in an inverted position (i.e. with the aerosol cannister 60 of the drug sloping upward). The device is conveniently held between the thumb, resting on depression 81 on the hood or knee-cap portion 80, and the tip of the fore-finger on the bottom of the pressurized aerosol cannister 60. A firm squeeze depresses the valve-stem of the aerosol cannister 60, delivering a dose of medication though the conduit 74 of the aerosol head 70 and out of the spray orifice 73.

DESCRIPTION OF THE PREFERRED EMBODIMENTS

The bioavailability of aerosolized peptides depends greatly upon the amount of the drug which is delivered to the deep lungs of a patient. As shown by the data in Table 1, the bioavailability of the LFLRH antagonist leuprolide acetate ranges widely with the depth to which the aerosolized drug is delivered to the deep lungs. Leuprolide was administered to tracheotomized dogs by aerosolizing the drug at various depths in the airway passage and then measuring the percentage of the drug which was absorbed into the dog's system as measured by blood levels of the drug. Intravenous injection of the drug was used as a control. The data are presented in Table 1 where blood levels achieved over time (AUC) are given. AUC is the integrated area under the curve of the plot of blood levels in ng/ml versus time.

As can be seen by the data presented there, when the drug was introduced at points ranging between approximately 5 to 20 cm below the epiglottis, there was incomplete absorption of the drug into the blood system of the dogs. However, when the drug was introduced at points ranging between about 20–25 cm below the epiglottis, absorption of the drug almost reached levels by intravenous administration.

TABLE 1

| Route of Administration | Distance Below the Epiglottis (cm) | AUC* (hr ng/ml) | Percent Bioavail- ibility |
| --- | --- | --- | --- |
| Intratracheal (N = 4) | 5–8 | 16.5 ± 31.2 | 6.8 |
| Intratracheal (N = 4) | 10–15 | 18.6 ± 35.6 | 4.6 |
| Intratracheal (n = 4) | 15–20 | 203.7 ± 46.0 | 50.3 |
| Intratracheal (N = 4) | 20–25 | 385.0 ± 25.9 | 95.0 |
| Intravenous (N = 6) |  | 405.1 ± 58.4 | 100.0 |

*AUC is the integrated area under the curve for the plot of blood level vs. time It is known that aerosolized particles will deposit in various parts of the human airway passage depending upon their aerodynamic particle size (diameter). Generally, particles of a size below about 4.5 μM will deposit in the deep lungs. Particles of a size greater than about 4.7 μM will deposit in the delivery device, the throat, and the trachea where bioabsorption of the drug is greatly diminished.

It has been found that there are certain critical features of the aerosol inhalation device of the present invention which affect the efficiency of drug delivery to the lungs of a patient. In particular the angle of orientation between the central axes of the cannister-receiving portion 40 and the expansion chamber 30 is preferably between about 102° and 110°, most preferably about 105°. The data in Table 2 show the dependency of the efficiency of drug delivery of devices in accordance with the present invention on the angle between major central axes of the cannister-receiving portion 40 and the expansion chamber 30.

TABLE 2

| Angle Between the the Central Axis of the Cannister-Receiving Portion and the Central Axis of the Expansion Chamber | Percent Delivery of Medication |
| --- | --- |
| 90° | 36% |
| 105° | 50% |
| 110° | 45% |

Moreover, the eccentricity of the elliptical cross-section of the expansion chamber has been found to be important in affecting the efficiency of the device. As used throughout this specification and the appended claims, the term "eccentricity" means the ratio of the major axis, A, of the elliptical expansion chamber 30 as shown in FIG. 2 and the minor axis, B, As shown by the data in Table 3 for reasons not fully understood, variation of the eccentricity of cross-section of the expansion chamber caused variation in the percent of aerosol drug delivered. The preferred eccentricity of the elliptical cross-section of the expansion chamber portion 30 of aerosol inhalation devices of this invention ranges between about 0.5 and about 0.85, most preferably about 0.75.

TABLE 3

| Eccentricity of the Elliptical Expansion Chamber | Percent Delivery of Medication |
| --- | --- |
| 0.50 | 35% |
| 0.75 | 50% |
| 0.85 | 42% |
| 1.00 | 30% |

In addition, the total volume of the expansion chamber portion 30 affects the efficiency of drug delivery. While not holding to one theory to the exclusion of others, it is believed that when the volume of the chamber is too small, the aerosol particles delivered from the aerosol head orifice are still wetted by propellant when the particles enter the throat of a patient. This results in a higher degree of impact of the particles in the patient's throat with less drug being delivered to the deep lungs as desired. On the other hand, when the volume of the expansion chamber is too large, the aerosol particles are fully dried by evaporation in the expansion chamber of the device, but it is believed that agglomeration of the dried particles results in less delivery of the drug particles to the deep lungs of the patient.

In the aerosol inhalation device of the present invention, as shown by the data in Table 4, the preferred volume of the expansion chamber ranges between about 25 cm$^3$ and about 100 cm$^3$, most preferably about 50 cm$^3$.

TABLE 4

| Expansion Chamber Volume (cm$^3$) | Percent Delivery of Medication |
| --- | --- |
| 25 | 30 |
| 50 | 50 |
| 75 | 45 |
| 100 | 28 |
| 150 | 12 |

While there have been shown and described what are at present believed to be the preferred embodiments of the present invention, it will be clear to one of ordinary skill in the art that various modifications can be made therein without departing from the scope of the invention as it is defined by the appended claims.

We claim:

1. A collapsible articulated actuator liar the aerosol delivery of a medicament comprising an expansion chamber portion, and an aerosol medicament cannister-receiving portion being slideably receivable inside said expansion chamber and rotatably attached thereto;

said expansion chamber portion comprising an elliptical cylinder having first and second open ends, said first open end having mouthpiece means, and said second open end having hinging means for rotatably and slideably attaching said cannister-receiving portion, said elliptical expansion chamber having a cross-sectional eccentricity of between about 0.50 and about 0.85;

said medicament cannister-receiving portion comprising an elliptical cylinder having first and second open ends, said first open end having means for slideably receiving and engaging an aerosol cannister of medicament, and said second open end having cannister valve-stem receiving means, aerosol spray orifice means, means for slideably and rotatably attaching said cannister-receiving portion to said expansion chamber portion, and stop means for affixing the angle between said expansion chamber and said cannister-receiving portion;

whereby when said cannister-receiving portion is slideably extended out of said said expansion chamber and rotated annul said hinging means, the angle between the major axes of said cannister-receiving portion and said expansion chamber portion is fixed.

2. An actuator as defined by claim 1 wherein the cross-sectional eccentricity of the elliptical expansion chamber is about 0.75.

3. An actuator as defined by claim 1 wherein the angle between the major axes of said cannister-receiving portion and said expansion chamber when said actuator is in its fully extended and folded position for use ranges between about 102° and about 110°.

4. An actuator as defined by claim 3 wherein the angle between the major axes of said cannister-receiving portion and said expansion chamber when said actuator is in its fully extended and folded position for use is about 105°.

5. An actuator as defined by claim 1 wherein the volume of said expansion chamber ranges between about 25 $cm^3$ and about 100 $cm^3$.

6. An actuator as defined by claim 5 wherein the volume of mid expansion chamber is about 50 $cm^3$.

7. A collapsible articulated actuator for the aerosol delivery, of a medicament comprising an expansion chamber portion, and an aerosol medicament cannister-receiving portion being slideably receivable inside said expansion chamber and rotatably attached thereto;

said expansion chamber portion comprising an elliptical cylinder having an eccentricity ranging between about 0.50 and about 0.85 and a volume ranging between about 25 $cm^3$ and 100 $cm^3$ and having first and second open ends said first open end having mouthpiece means, and said second open end having hinging means for rotatably and slideably attaching said cannister-receiving portion; and said medicament cannister-receiving portion comprising an elliptical cylinder having first and second open ends, said first open end having means for slideably receiving and engaging an aerosol cannister of medicament, and said second open end having cannister valve-stem receiving means, aerosol spray orifice means, means for slideably and rotatably attaching said cannister-receiving portion to said expansion chamber portion, and stop means for affixing the angle between said expansion chamber and said cannister-receiving portion;

whereby when said cannister-receiving portion is slideably extended out of said expansion chamber and rotated about said hinging means the angle between the major axes of said cannister-receiving portion and said expansion chamber portion is fixed at about 102° to about 110°.

8. An actuator as defined by claim 7 wherein the cross-sectional eccentricity of the elliptical expansion chamber is about 0.75.

9. An actuator as defined by claim 7 wherein the volume of said expansion chamber is about 50 $cm^3$.

10. An actuator as defined by claim 7 wherein the angle between the major axes of said cannister-receiving portion and said expansion chamber when said actuator is in its fully extended and folded position for use is about 105°.

* * * * *

UNITED STATES PATENT AND TRADEMARK OFFICE
CERTIFICATE OF CORRECTION

PATENT NO. : 5,505,194
DATED : April 9, 1996
INVENTOR(S) : A. L. Adjei, et al.

It is certified that error appears in the above-indentified patent and that said Letters Patent is hereby corrected as shown below:

Column 3, line 10, change "or" to --of--.

Column 3, line 53, change "sloes" to --slots--.

Column 5, line 17, change "LFLRH" to --LHRH--.

Column 7, line 33, change "annul" to --about--.

Column 8, line 5, change "mid" to --said--.

Signed and Sealed this

Eighth Day of October, 1996

*Attest:*

BRUCE LEHMAN

*Attesting Officer    Commissioner of Patents and Trademarks*